United States Patent
Bao et al.

(10) Patent No.: US 11,192,846 B2
(45) Date of Patent: Dec. 7, 2021

(54) PREPARATION METHOD OF SUBSTITUTED PRIMARY AMINE

(71) Applicant: DALIAN UNIVERSITY OF TECHNOLOGY, Liaoning (CN)

(72) Inventors: Ming Bao, Liaoning (CN); Xiujuan Feng, Liaoning (CN); Ye Lu, Liaoning (CN); Xiaoqiang Yu, Liaoning (CN); Sheng Zhang, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 16/981,113

(22) PCT Filed: Aug. 5, 2019

(86) PCT No.: PCT/CN2019/099185
§ 371 (c)(1),
(2) Date: Sep. 15, 2020

(87) PCT Pub. No.: WO2020/057274
PCT Pub. Date: Mar. 26, 2020

(65) Prior Publication Data
US 2021/0017119 A1    Jan. 21, 2021

(30) Foreign Application Priority Data
Sep. 20, 2018 (CN) .......................... 201811098513.5

(51) Int. Cl.
*C07C 209/26* (2006.01)

(52) U.S. Cl.
CPC .................. *C07C 209/26* (2013.01)

(58) Field of Classification Search
None
See application file for complete search history.

(56) References Cited

U.S. PATENT DOCUMENTS

2016/0279619 A1* 9/2016 Sun ..................... B01J 35/006

OTHER PUBLICATIONS

P. W. Selwood. Magnetism and the Structure of Catalytically Active Solids. Adv. Catal., 1951, 3, 27-106.*

(Continued)

*Primary Examiner* — Clinton A Brooks
(74) *Attorney, Agent, or Firm* — Muncy, Geissler, Olds & Lowe, P.C.

(57) ABSTRACT

A preparation method of substituted primary amine is disclosed. The preparation method uses cyanophenyl and a derivative thereof as raw materials, nanoporous palladium as a catalyst, and $H_2$ as a hydrogen source, and conducts selective hydrogenation to prepare the substituted primary amine. The molar concentration of the cyanophenyl and the derivative thereof in the solvent is 0.01-2 mmol/mL, and the molar ratio of the cyanophenyl to the derivative thereof to the catalyst is 1:0.01-1:0.5. The size of a pore framework of the nanoporous palladium is 1 nm-50 nm. The pressure of the $H_2$ is 0.1-20.0 MPa. The obtained product has high selectivity; the present invention has mild reaction conditions, does not need any additive, and has simple operation and post-processing and good catalyst reproducibility. After repeatedly used, the catalytic activity of the present invention is not significantly reduced, thereby providing the possibility of realizing industrialization.

3 Claims, 5 Drawing Sheets

(56) References Cited

OTHER PUBLICATIONS

F. Solymosi. Importance of the Electric Properties of Supports in the Carrier Effect. Catal. Rev., 1967, 1, 233-255.*

S. J. Tauster, S. C. Fung, R. T. K. Baker, J. A. Horsley. Strong Interactions in Supported-Metal Catalysts. Science, 1981, 211, 1121-1125.*

S. J. Tauster, S. C. Fung, R. L. Garten. Strong Metal-Support Interactions: Group 8 Noble Metals Supported on TiOz. JACS, 1978, 100, 170-175.*

S. J. Tauster. Strong Metal-Support Interactions. Acc. Chem. Res., 1987, 20, 389-394.*

W. H. Hartung. Catalytic Reduction of Nitriles and Oximes./. Am. Chem. Soc., 1928, 50, 3370-3374.*

S. P. Bawane, S. B. Sawant. Reaction Kinetics of the Liquid-Phase Hydrogenation of Benzonitrile to Benzylamine Using Raney Nickel Catalyst. Chem. Eng. J., 2004, 103, 13-19.*

C. F. Winans. Hydrogenation of Aldehydes in the Presence of Ammonia./. Am. Chem. Soc., 1939, 61, 3566-3567.*

S. Gomez, J. A. Peters, T. Maschmeyer. The Reductive Amination of Aldehydes and Ketones and the Hydrogenation of Nitriles: Mechanistic Aspects and Selectivity Control. Adv. Synth. Catal., 2002, 344, 1037-1057.*

D. Formenti, R. Mocci, H. Atia, S. Dastgir, M. Anwar, S. Bachmann, M. Scalone, K. Junge, M. Beller. A State-of-the-Art Heterogeneous Catalyst for Efficient and General Nitrile Hydrogenation. Chem.—Eur. J., 2020, 26, 15589-15595.*

T. Mitsudome, M. Sheng, A. Nakata, J. Yamasaki, T. Mizugaki, K. Jitsukawa. A Cobalt Phosphide Catalyst for the Hydrogenation of Nitriles. Chem. Sci., 2020, 11, 6682-6689.*

M. Hoogenraad, J. B. van der Linden, A. A. Smith. Accelerated Process Development of Pharmaceuticals: Selective Catalytic Hydrogenations of Nitro Compounds Containing Other Functionalities. Org. Process Res. Dev., 2004, 8, 469-476.*

M. Urushizaki, H. Kitazawa, S. Takano, R. Takahata, S. Yamazoe, T. Tsukuda. Synthesis and Catalytic Application of Ags4 Clusters Supported on Mesoporous Carbon. J. Phys. Chem. C, 2015, 119, 27483-27488.*

Search Report issued in corresponding International application No. PCT/CN2019/099185 dated Nov. 6, 2019 (with English translation attached).

Written Opinion issued in corresponding International application No. PCT/CN2019/099185 dated Nov. 6, 2019.

* cited by examiner

PREPARATION METHOD OF SUBSTITUTED PRIMARY AMINE

TECHNICAL FIELD

The present invention belongs to the technical field of medicine and natural compound chemical intermediates and related chemistry, and relates to a preparation method of substituted aliphatic primary amine.

BACKGROUND

Selective reduction of nitrile to prepare primary aliphatic amine is a very important step in organic synthesis. Especially in the synthesis of some important high-value compounds (such as bioactive molecules, natural products and other industrial materials of important natural products), the synthesis of high-purity primary aliphatic amine is a key step.

The traditional methods for preparing the primary aliphatic amine by selective reduction of the nitrile are mainly classified into two categories. One category is a homogeneous catalyst combining Ru, Ir, Co, Fe and other transition metals with ligands. Although this category of catalyst has high activity, it has many disadvantages, such as poor selectivity and the formation of more by-products, i.e., secondary amine and tertiary amine Secondly, very high temperature and pressure (T>120° C. and $H_2$>50 bar) are often required, and the catalyst is expensive, difficult to separate and recover, and not reusable [REGUILLO R, GRELLIER M, VAUTRAVERS N, et al. *J. Am. Chem. Soc.* 2010, 132, 7854-7855; BORNSCHEIN C, WERKMEISTER S, WENDT B, MAO H, et al. *Nat. Commun.* 2014, 5, 4111; MUKHERJEE A, SRIMANI D, CHAKRABORTY S, MILSTEIN D, et al. *J. Am. Chem. Soc.* 2015, 137, 8888-8891.]. The second category is a heterogeneous catalyst which is researched much. Such catalyst includes Raney nickel, Raney cobalt, and the like. However, it is common for the catalyst to be sensitive and extremely unstable, which is very dangerous. The use of a large amount of additive base ($NH_3$) to improve the selectivity of the reaction limits the industrial application [DE BELLEFON C, FOUILLOUX P. *Catal. Rev.: Sci. Eng.* 1994, 36, 459; NISHIMURA S, Handbook of Hetergogeneous Catalytic Hydrogenation for Organic Synthesis; John Wiley & Sons: New York, 2001; p 254; BLASER H U, MALAN C, PUGIN B, SPINDLER F, et al. *Adv. Synth. Catal.* 2003, 345, 103-151.]. Nanoporous palladium material is a new type of nano-structure catalyst which is composed of nano-scale pores and ligaments. Compared with most metals, the nanoporous palladium material has a large specific surface area, excellent electrical and thermal conductivity, and non-toxic performance, can exhibit physical and chemical properties completely different from bulk metals, and has been widely concerned in the field of catalysis research. A nanoporous palladium catalyst (PdNPore) has the advantages of high catalytic activity, stability, and convenient recycling [TANAKA S, KANEKO T, ASAO N, YAMAMOTO Y, CHEN M-W, ZHANG W, INOUE A. *Chem. Commun.*, 2011, 47, 5985-5987; KANEKO T, TANAKA S, ASAO N, YAMAMOTO Y, et al. *Adv. Synth. Catal.*, 2011, 353, 2927-2932.].

SUMMARY

In order to solve the above problems, the present invention provides a preparation method of substituted primary aliphatic amine. The method has mild reaction conditions, does not need any additive, and has selectivity of 100%. The selected catalyst has the advantages of high activity and good stability. After repeatedly used, the catalytic activity of the catalyst is not significantly reduced.

The technical solution of the present invention:

A preparation method of substituted primary aliphatic amine uses benzonitrile and a derivative thereof as raw materials, nanoporous palladium (PdNPore) as a catalyst, and $H_2$ as a hydrogen source, and conducts selective hydrogenation to prepare the substituted primary aliphatic amine A synthetic route is shown as follows:

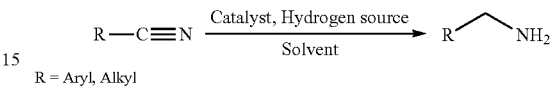

R = Aryl, Alkyl

Reaction temperature is 0° C.-150° C., and reaction time is 12 h-36 h.

R is aryl or alkyl.

The solvent is one or a mixture of more than one of water, ether, acetonitrile, dimethyl sulfoxide, dioxane, triethylamine, tetrahydrofuran, toluene, ethanol, isopropanol, chloroform, methylene chloride, acetone and N, N-dimethylformamide.

The molar concentration of the benzonitrile and the derivative thereof in the solvent is 0.01-2 mmol/mL, and the molar ratio of the benzonitrile to the derivative thereof to the catalyst is 1:0.01-1:0.5.

The size of a pore framework of the nanoporous palladium is 1 nm-50 nm.

The pressure of the $H_2$ is 0.1-20.0 MPa.

Separation methods comprise recrystallization, column chromatography, etc. The solvent used in the recrystallization method may be chloroform, cyclohexane, dioxane, benzene, toluene, ethanol, petroleum ether, acetonitrile, N, N-dimethylformamide, tetrahydrofuran and ethyl acetate. The column chromatography method can use silica gel or basic alumina as a stationary phase, and use a mixture of polar and nonpolar solvents as an eluent, such as ethyl acetate-petroleum ether, ethyl acetate-hexane, dichloromethane-petroleum ether, methanol-petroleum ether and methanol-ethyl acetate.

The beneficial effects of the present invention are: the method of the present invention has mild reaction conditions, does not need any additive, and has high product selectivity, simple operation and post-processing and good catalyst reproducibility. After repeatedly used, the catalytic activity of the method is not significantly reduced, thereby providing the possibility of realizing industrialization.

DETAILED DESCRIPTION

Figure 1:
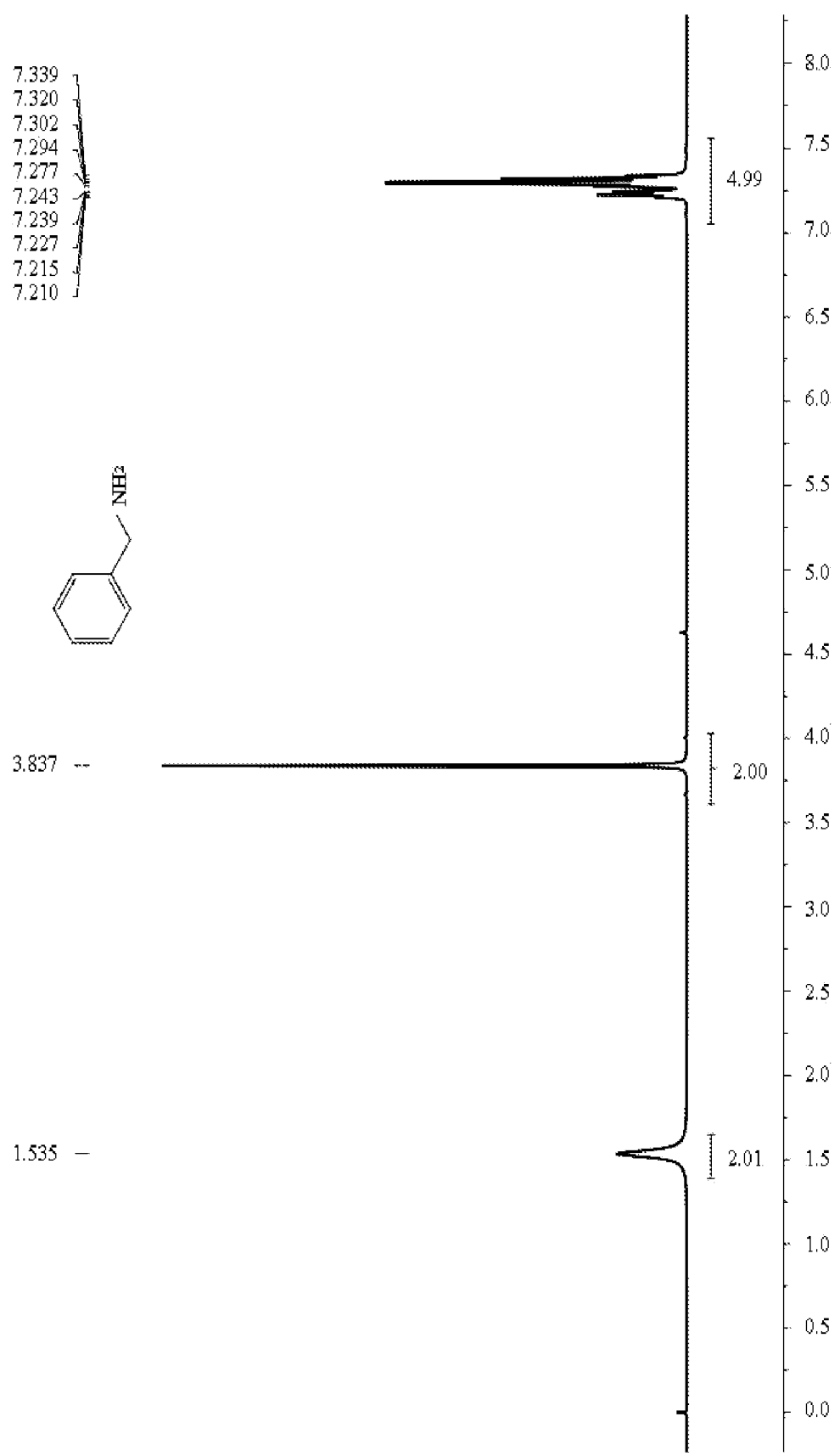
FIG. 1 is a $^1$H NMR spectrum diagram of benzylamine in embodiments 1 and 2.
Figure 2:
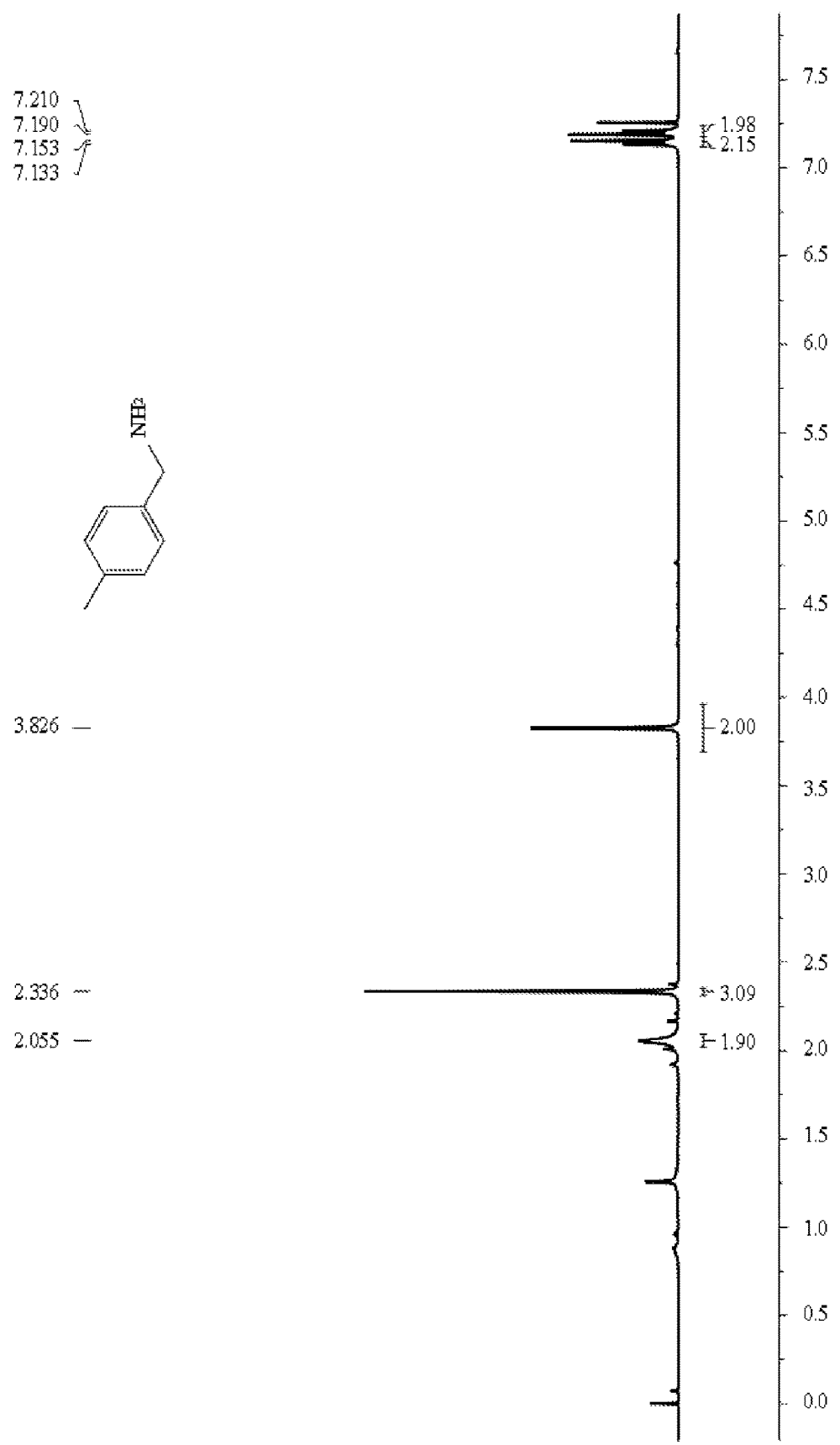
FIG. 2 is a $^1$H NMR spectrum diagram of 4-methylbenzylamine in embodiments 3 and 4.
Figure 3:
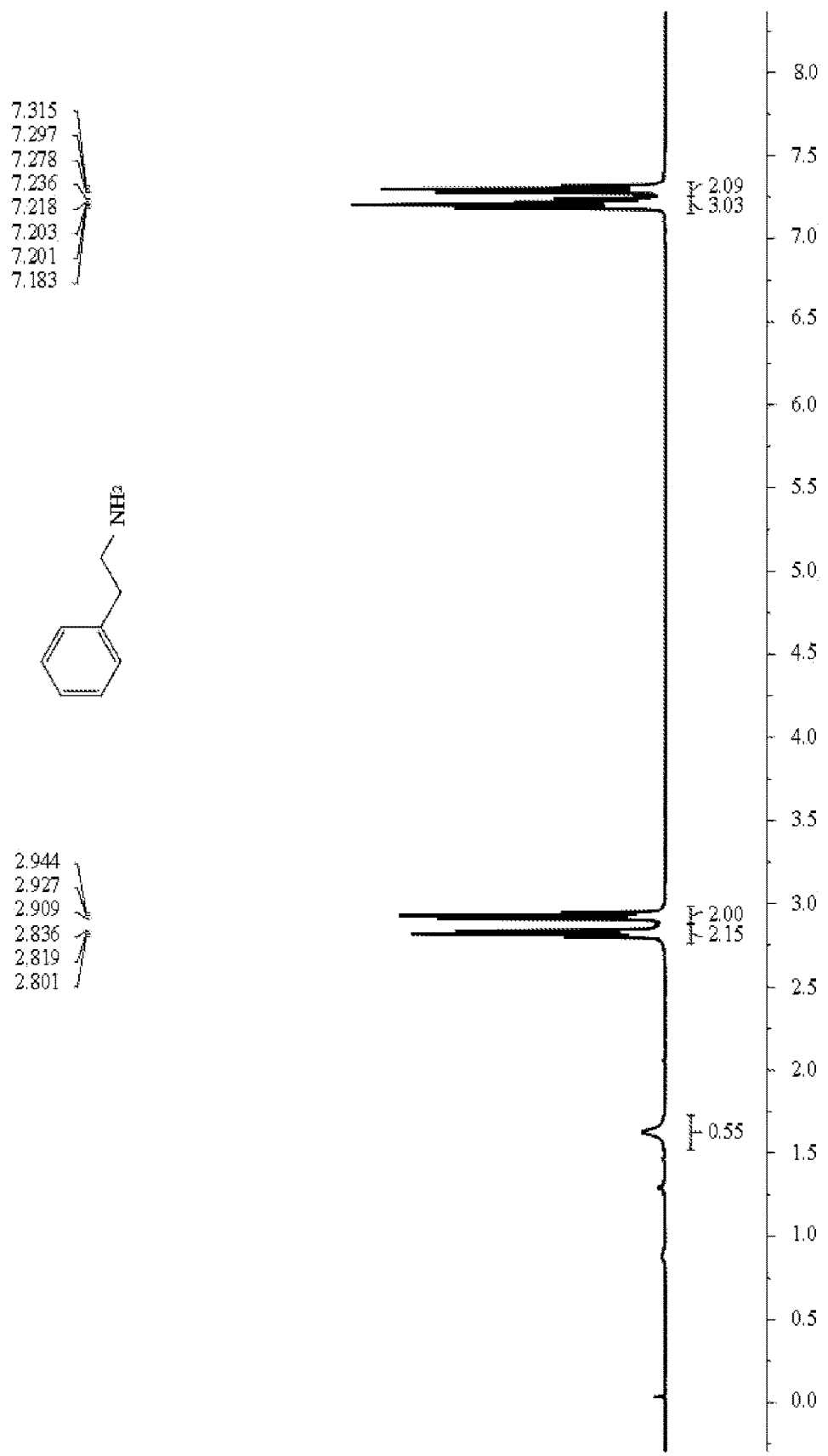
FIG. 3 is a $^1$H NMR spectrum diagram of phenethylamine in embodiments 5 and 6.
Figure 4:
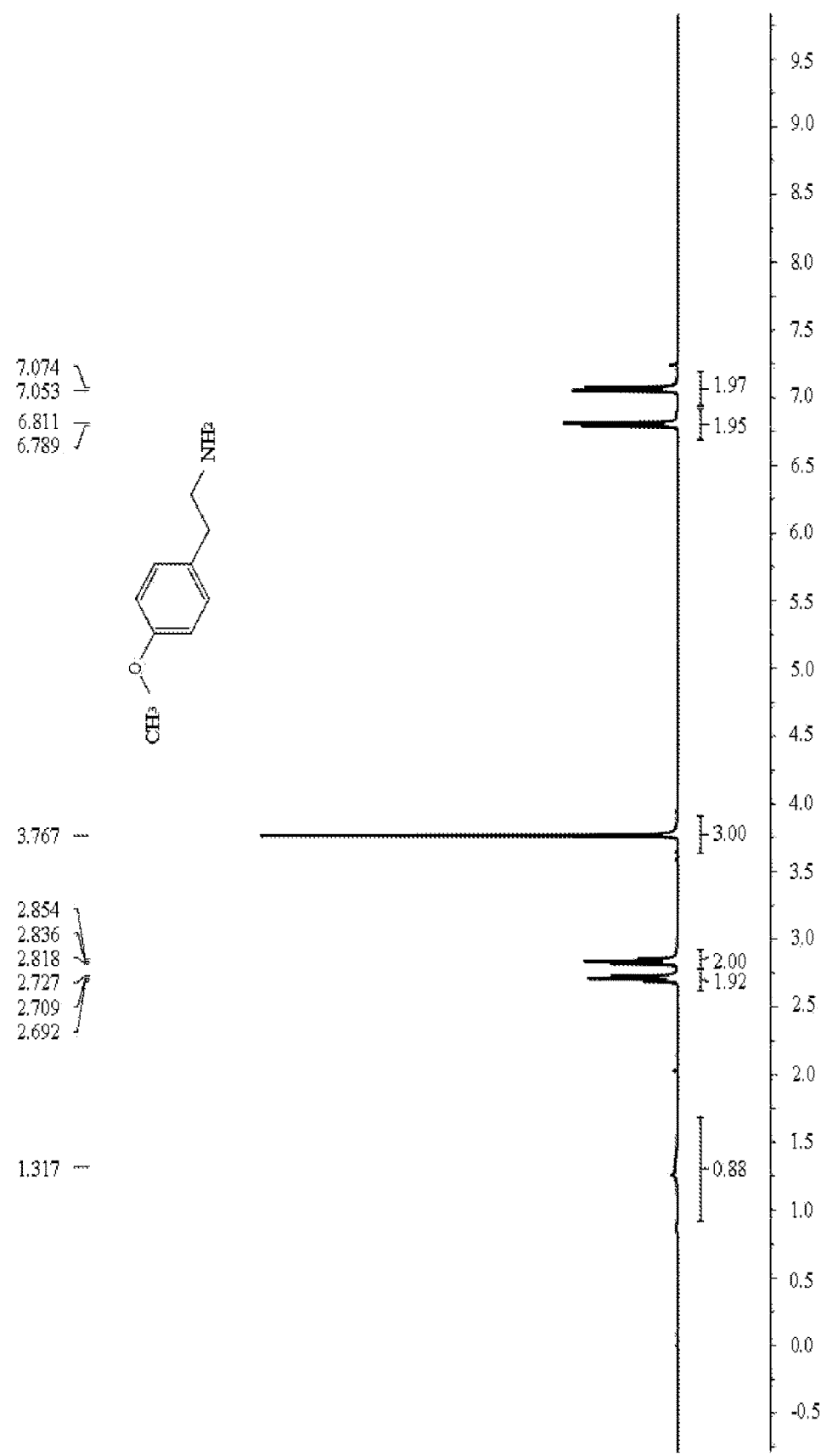
FIG. 4 is a $^1$H NMR spectrum diagram of 4-methoxyphenethylamine in embodiments 7 and 8.
Figure 5:
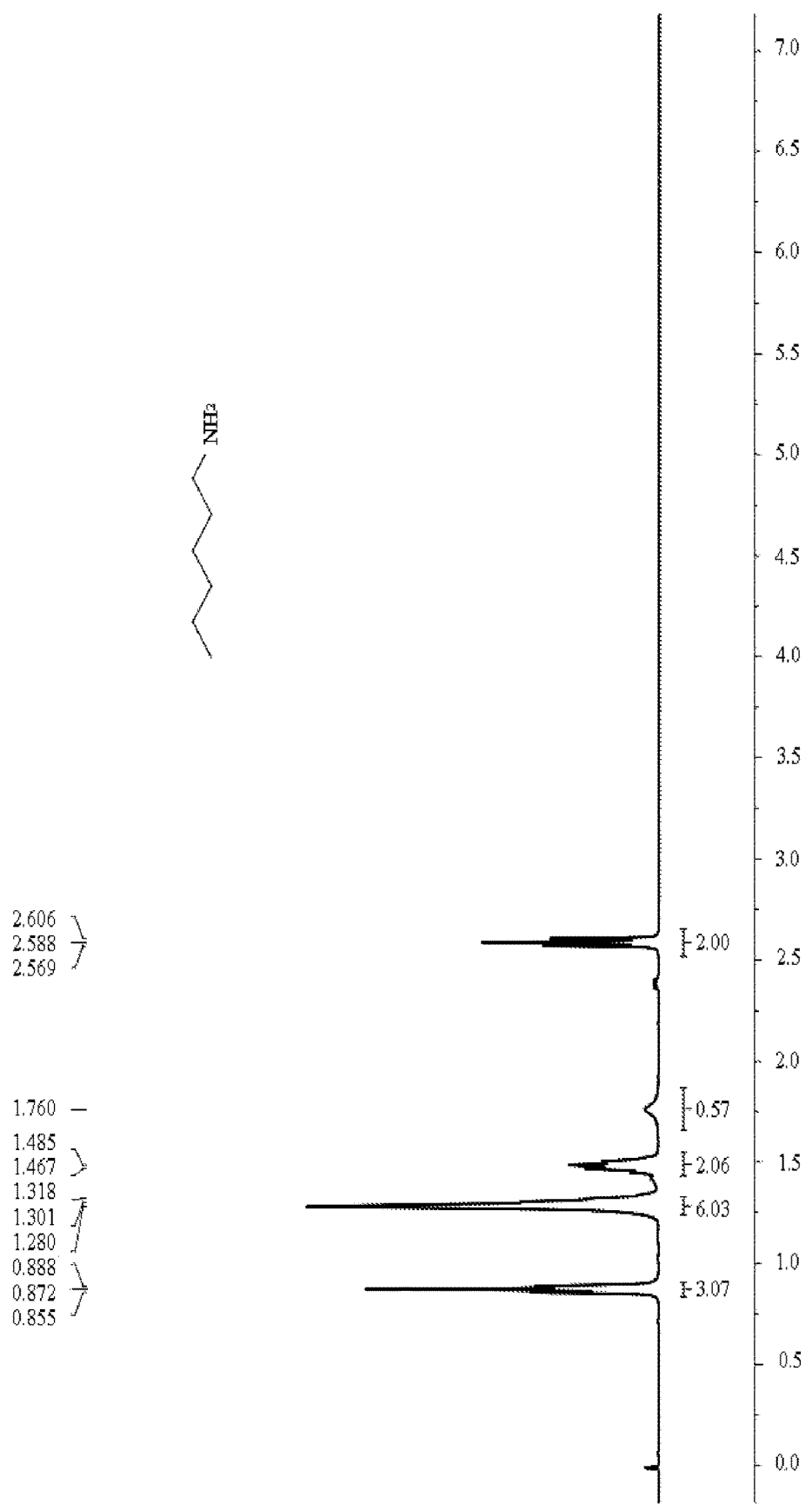
FIG. 5 is a $^1$H NMR spectrum diagram of n-hexylamine in embodiments 9 and 10.

Specific embodiments of the present invention are further described below in combination with accompanying drawings and the technical solution.

The preparation method of the substituted primary aliphatic amine in the present invention has highest selectivity and reaction yield of 100% and 93% respectively, and does not need any additive in the reaction. The selected catalyst has good catalytic reaction reproducibility and simple operation and post-processing. After repeatedly used, the catalytic activity of the catalyst is not significantly reduced, thereby providing favorable conditions for the industrial production.

Embodiment 1: Synthesis of Benzylamine

A substrate benzonitrile (51.6 mg, 0.5 mmol) and hydrogen (5 bar) are added to an ethanol (3 mL) solvent with PdNPore (1.6 mg, 3 mol %) catalyst; the mixture is placed in an oil bath at 50° C. to react for 24 h; column chromatography is conducted (silica gel, 200-300 meshes; developing agent, methanol and ethyl acetate) to obtain 48.8 mg of benzylamine, with yield of 93% and selectivity of 97%. Under the same conditions, if Pd/C is used as the catalyst, the yield of the benzylamine is only 65%, and the selectivity is 72%.

benzylamine $^1$H NMR (400 MHz, CDCl$_3$) δ: 7.35-7.20 (m, 5H), 3.84 (s, 2H), 1.54 (br, 2H).

Embodiment 2: Synthesis of Benzylamine

A substrate benzonitrile (30.9 mg, 0.3 mmol) and hydrogen (5 bar) are added to an N,N-dimethylformamide (3 mL) solvent with PdNPore (5.4 mg, 10 mol %) catalyst; the mixture is placed in an oil bath at 30° C. to react for 20 h; column chromatography is conducted (silica gel, 200-300 meshes; developing agent, methanol and ethyl acetate) to obtain 28.9 mg of benzylamine, with yield of 90% and selectivity of 96%.

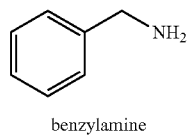

benzylamine $^1$H NMR (400 MHz, CDCl$_3$) δ: 7.35-7.20 (m, 5H), 3.84 (s, 2H), 1.54 (br, 2H).

Embodiment 3: Synthesis of 4-methylbenzylamine

A substrate 4-methylbenzonitrile (58.6 mg, 0.5 mmol) and hydrogen (5 bar) are added to an ethanol (3 mL) solvent with PdNPore (1.6 mg, 3 mol %) catalyst; the mixture is placed in an oil bath at 50° C. to react for 24 h; column chromatography is conducted (silica gel, 200-300 meshes; developing agent, methanol and ethyl acetate) to obtain 53.9 mg of 4-methylbenzylamine, with yield of 89% and selectivity of 98%. Under the same conditions, if Pd/C is used as the catalyst, the yield of the 4-methylbenzylamine is only 69%, and the selectivity is 78%.

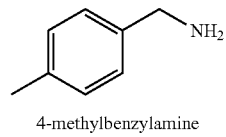

4-methylbenzylamine $^1$H NMR (CDCl$_3$, 400 MHz) δ: 7.20 (d, J=8 Hz, 2H), 7.14 (d, J=8 Hz, 2H), 3.83 (s, 2H), 2.34 (s, 3H), 2.06 (br, 2H).

Embodiment 4: Synthesis of 4-methylbenzylamine

A substrate 4-methylbenzonitrile (58.6 mg, 0.5 mmol) and hydrogen (5 bar) are added to an acetonitrile (5 mL) solvent with PdNPore (1.1 mg, 2 mol %) catalyst; the mixture is placed in an oil bath at 50° C. to react for 24 h; column chromatography is conducted (silica gel, 200-300 meshes; developing agent, methanol and ethyl acetate) to obtain 50.3 mg of 4-methylbenzylamine, with yield of 83% and selectivity of 96%.

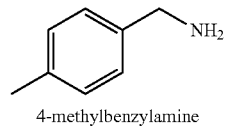

4-methylbenzylamine $^1$H NMR (CDCl$_3$, 400 MHz) δ: 7.20 (d, J=8 Hz, 2H), 7.14 (d, J=8 Hz, 2H), 3.83 (s, 2H), 2.34 (s, 3H), 2.06 (br, 2H).

Embodiment 5: Synthesis of Phenethylamine

A substrate phenylacetonitrile (58.58 mg, 0.5 mmol) and hydrogen (5 bar) are added to an ethanol (3 mL) solvent with PdNPore (1.6 mg, 3 mol %) catalyst; the mixture is placed in an oil bath at 70° C. to react for 24 h; column chromatography is conducted (silica gel, 200-300 meshes; developing agent, methanol and ethyl acetate) to obtain 53.3 mg of phenethylamine, with yield of 88% and selectivity of 100%. Under the same conditions, if Pd/C is used as the catalyst, the yield of the phenethylamine is only 40%, and the selectivity is 45%.

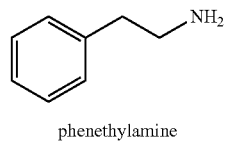

phenethylamine $^1$H NMR (400 MHz, CDCl$_3$) δ: 7.29-7.24 (m, 2H), 7.21-7.14 (m, 3H), 2.89 (t, J=7.2 Hz, 2H), 2.78 (t, J=7.2 Hz, 2H), 1.59 (br, 2H).

Embodiment 6: Synthesis of Phenethylamine

A substrate phenylacetonitrile (58.58 mg, 0.5 mmol) and hydrogen (5 bar) are added to an ethanol (5 mL) solvent with PdNPore (2.7 mg, 5 mol %) catalyst; the mixture is placed in an oil bath at 70° C. to react for 19 h; column chromatography is conducted (silica gel, 200-300 meshes; developing agent, methanol and ethyl acetate) to obtain 52.71 mg of phenethylamine, with yield of 87% and selectivity of 100%.

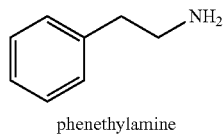

phenethylamine $^1$H NMR (400 MHz, CDCl$_3$) δ: 7.29-7.24 (m, 2H), 7.21-7.14 (m, 3H), 2.89 (t, J=7.2 Hz, 2H), 2.78 (t, J=7.2 Hz, 2H), 1.59 (br, 2H).

Embodiment 7: Synthesis of 4-Methoxyphenethylamine

A substrate 4-methoxybenzeneacetonitrile (73.59 mg, 0.5 mmol) and hydrogen (5 bar) are added to an ethanol (3 mL) solvent with PdNPore (1.6 mg, 3 mol %) catalyst; the mixture is placed in an oil bath at 70° C. to react for 24 h; column chromatography is conducted (silica gel, 200-300 meshes; developing agent, methanol and ethyl acetate) to obtain 62.8 mg of 4-methoxyphenethylamine, with yield of 83% and selectivity of 100%.

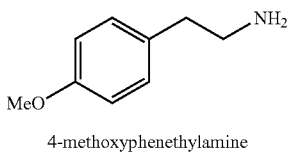 [SMILES: COc1ccc(CCN)cc1]

4-methoxyphenethylamine $^1$H NMR (400 MHz, CDCl$_3$) δ: 7.06 (d, J=8 Hz, 2H), 6.80 (d, J=8 Hz, 2H), 3.77 (s, 3H), 2.84 (t, J=8 Hz, 2H), 2.71 (t, J=8 Hz, 2H).

Embodiment 8: Synthesis of 4-methoxyphenethylamine

A substrate 4-methoxybenzeneacetonitrile (73.59 mg, 0.5 mmol) and hydrogen (5 bar) are added to an acetonitrile (5 mL) solvent with PdNPore (2.7 mg, 5 mol %) catalyst; the mixture is placed in an oil bath at 50° C. to react for 16 h; column chromatography is conducted (silica gel, 200-300 meshes; developing agent, methanol and ethyl acetate) to obtain 60.48 mg of 4-methoxyphenethylamine, with yield of 80% and selectivity of 98%.

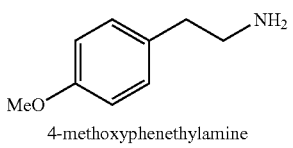 [SMILES: COc1ccc(CCN)cc1]

4-methoxyphenethylamine $^1$H NMR (400 MHz, CDCl$_3$) δ: 7.06 (d, J=8 Hz, 2H), 6.80 (d, J=8 Hz, 2H), 3.77 (s, 3H), 2.84 (t, J=8 Hz, 2H), 2.71 (t, J=8 Hz, 2H).

Embodiment 9: Synthesis of n-hexylamine

A substrate hexanenitrile (48.58 mg, 0.5 mmol) and hydrogen (5 bar) are added to an ethanol (3 mL) solvent with PdNPore (1.6 mg, 3 mol %) catalyst; the mixture is placed in an oil bath at 50° C. to react for 24 h; column chromatography is conducted (silica gel, 200-300 meshes; developing agent, methanol and ethyl acetate) to obtain 44.0 mg of n-hexylamine, with yield of 87% and selectivity of 100%.

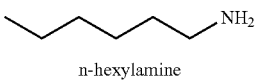

n-hexylamine $^1$H NMR (400 MHz, CDCl$_3$) δ: 2.60 (t, J=7.2 Hz, 2H), 1.77 (br, 2H), 1.52-1.46 (m, 2H), 1.36-1.28 (m, 6H), 0.88 (t, J=6.8 Hz, 3H).

Embodiment 10: Synthesis of n-hexylamine

A substrate hexanenitrile (48.58 mg, 0.5 mmol) and hydrogen (6 bar) are added to an ethanol (3 mL) solvent with PdNPore (2.7 mg, 5 mol %) catalyst; the mixture is placed in an oil bath at 80° C. to react for 20 h; column chromatography is conducted (silica gel, 200-300 meshes; developing agent, methanol and ethyl acetate) to obtain 45.54 mg of n-hexylamine, with yield of 90% and selectivity of 100%.

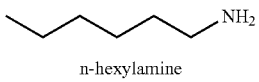

n-hexylamine $^1$H NMR (400 MHz, CDC$_3$) δ: 2.60 (t, J=7.2 Hz, 2H), 1.77 (br, 2H), 1.52-1.46 (m, 2H), 1.36-1.28 (m, 6H), 0.88 (t, J=6.8 Hz, 3H).

The invention claimed is:

1. A method for preparing a substituted primary amine comprising:
   hydrogenating a cyanophenyl or cyanoalkyl raw materials in the presence of an unsupported nanoporous palladium catalyst, and H$_2$ as a hydrogen source; and
   conducting selective hydrogenation to prepare the substituted primary amine, wherein a synthetic route is shown as follows:

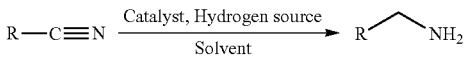

R = Aryl, Alkyl reaction temperature is 0° C.-150° C., and reaction time is 12 h-36 h;
   R is aryl or alkyl;
   the solvent is one or a mixture of more than one of water, ether, acetonitrile, dimethyl sulfoxide, dioxane, triethylamine, tetrahydrofuran, toluene, ethanol, isopropanol, chloroform, methylene chloride, acetone and N,N-dimethylformamide,
   wherein a molar concentration of the cyanophenyl or cyanoalkyl in the solvent is 0.01-2 mmol/mL, and the molar ratio of the catalyst is 1:0.01-1:0.5.

2. The method for preparing the substituted primary amine according to claim 1, wherein a size of a pore framework of the unsupported nanoporous palladium is 1 nm-50 nm.

3. The method for preparing the substituted primary amine according to claim 1, wherein a pressure of the H$_2$ is 0.1-20.0 MPa.

* * * * *